(12) United States Patent
Mehlberg et al.

(10) Patent No.: US 7,119,243 B2
(45) Date of Patent: Oct. 10, 2006

(54) ALKYLATION PROCESS WITH EFFICIENT EFFLUENT REFRIGERATION

(75) Inventors: Robert L. Mehlberg, Wheaton, IL (US); Dale J. Shields, Buffalo Grove, IL (US); John J. Senetar, Naperville, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 11/100,209

(22) Filed: Apr. 6, 2005

(65) Prior Publication Data
US 2005/0197516 A1 Sep. 8, 2005

Related U.S. Application Data

(63) Continuation of application No. 10/172,297, filed on Jun. 12, 2002, now Pat. No. 6,943,276.

(51) Int. Cl.
*C07C 2/62* (2006.01)

(52) U.S. Cl. ............... 585/715; 585/719; 585/721; 585/723

(58) Field of Classification Search ........... 585/715, 585/719, 721, 723
See application file for complete search history.

(56) References Cited

U.S. PATENT DOCUMENTS

| | | | |
|---|---|---|---|
| 2,977,397 A | 3/1961 | Putney | 585/715 |
| 5,276,245 A | 1/1994 | Eastman et al. | 585/823 |
| 5,672,798 A | 9/1997 | Zhang et al. | 585/467 |
| 5,750,818 A | 5/1998 | Mehlberg et al. | 585/709 |

OTHER PUBLICATIONS

Chang, E.J.; *Alkylation of Motor Fuels* Process Economics Program Report No. 88A SRI International, Menlo Park, California, Feb. 1993.

*Primary Examiner*—Thuan Dinh Dang
(74) *Attorney, Agent, or Firm*—John G. Tolomei; Michael A. Moore

(57) ABSTRACT

An alkylation process in which a recycle stream is cooled by heat exchange with the alkylation reactor effluent is disclosed.

12 Claims, 2 Drawing Sheets

ALKYLATION PROCESS WITH EFFICIENT EFFLUENT REFRIGERATION

CROSS-REFERENCE TO RELATED APPLICATION

This application is a continuation of U.S. application Ser. No. 10/172,297, filed Jun. 12, 2002 now U.S. Pat. No. 6,943,276, the teachings of which are hereby incorporated in their entirety herein by reference.

FIELD OF THE INVENTION

This invention relates generally to a process for the alkylation of an alkylation substrate with an alkylating agent. This invention relates specifically to the separation and heat exchange of the alkylation effluent.

BACKGROUND OF THE INVENTION

The alkylation of an alkylation substrate (e.g., isoparaffin) with an alkylating agent (e.g., olefin) is an exothermic reaction. Commercially it is practiced using a catalyst at relatively low temperatures, which helps raise the yield of alkylate, the valuable product. The optimum alkylation temperature depends on many factors including the choice of catalyst, but alkylation reactors generally run in the range of −50 to 100° C. (−58 to 212° F.). The alkylation reactor effluent is usually in that temperature range too. Thus, the effluent poses a unique technical challenge in three aspects—to recover the product alkylate, to utilize the heat released by the alkylation reaction, and to recycle reactants to the reactor at a suitable low temperature.

Prior art alkylation units try to meet this challenge by flashing the reactor effluent. This produces a vapor that contains mostly unreacted alkylation substrate. This vapor is then used like a refrigerant is used in a refrigeration system; indeed, it is commonly called "refrigerant". It is compressed, condensed, and then flashed. These steps provide a stream which is both coolant and reactant. It is, therefore, well-suited for recycling to the reactor.

Unfortunately, the prior art units don't work well when the vapor contains light components don't condense at conventional condensation conditions. These components often include (but are not limited to) hydrogen, hydrogen chloride, methane, and ethane. They are commonly called "noncondensables," even though they most certainly will condense at very high pressure, if the temperature is low enough. But compressing the refrigerant in an alkylation process to that high of a pressure is prohibitively expensive. The costs of high-pressure equipment and utilities are simply too great.

Therefore, efficient methods are sought to recover alkylate, use the heat of reaction, and recycle unreacted alkylation substrate.

SUMMARY OF THE INVENTION

An alkylation process wherein the refrigerant is cooled by heat exchange with the alkylation reactor effluent is disclosed. This process has several advantages. One in particular occurs when the effluent contains components that do not condense at conventional condensation conditions to be recycled to the alkylation reactor. This is the case when the alkylation catalyst comprises chloride and the effluent contains hydrogen chloride. Then, the process disclosed herein helps to recycle light components such as hydrogen chloride and to cut hydrogen chloride losses, without excessive compression costs. This process is also useful when direct cooling of the alkylation reactor using reactor effluent is not practical because of the design of the alkylation reactor and/or the properties of the reactor effluent.

In one embodiment, this invention is an alkylation process. An alkylation substrate is alkylated with an alkylating agent in a reactor to form alkylate. A reactor effluent comprising the alkylate and the alkylation substrate is recovered from the reactor. At least a portion of the reactor effluent is flashed to form a refrigerant exchanger feed comprising the alkylate and the alkylation substrate. At least a portion of the refrigerant exchanger feed is heated in a refrigerant heat exchanger. A refrigerant exchanger effluent comprising the alkylate and the alkylation substrate is recovered from the refrigerant heat exchanger. At least a portion of the refrigerant exchanger effluent is passed to an effluent vapor-liquid separator. A vapor phase comprising the alkylation substrate and a liquid phase comprising the alkylate are recovered from the effluent vapor-liquid separator. The vapor phase is compressed to form a compressed stream comprising the alkylation substrate. At least a portion of the compressed stream is at least partially condensed to form a condensed stream comprising the alkylation substrate. In the refrigerant heat exchanger, heat is indirectly exchanged from at least a portion of the condensed stream to the at least a portion of the refrigerant exchanger feed in order to form a chilled recycle stream comprising the alkylation substrate. At least a portion of the chilled recycle stream is recycled to the reactor. The alkylate is recovered from the liquid phase.

Additional embodiments and advantages of this invention are described in the detailed description.

INFORMATION DISCLOSURE

U.S. Pat. No. 5,750,818 (Mehlberg et al.) describes an alkylation process for cooling unreacted hydrocarbon substrate that is recycled to an alkylation reactor.

Process Economics Program Report No. 88A, Alkylation of Motor Fuels (February 1993) by Elaine J. Chang, SRI International, Menlo Park, Calif., describes alkylation processes that employ sulfuric acid and autorefrigeration.

DETAILED DESCRIPTION OF THE INVENTION

Figure 1:
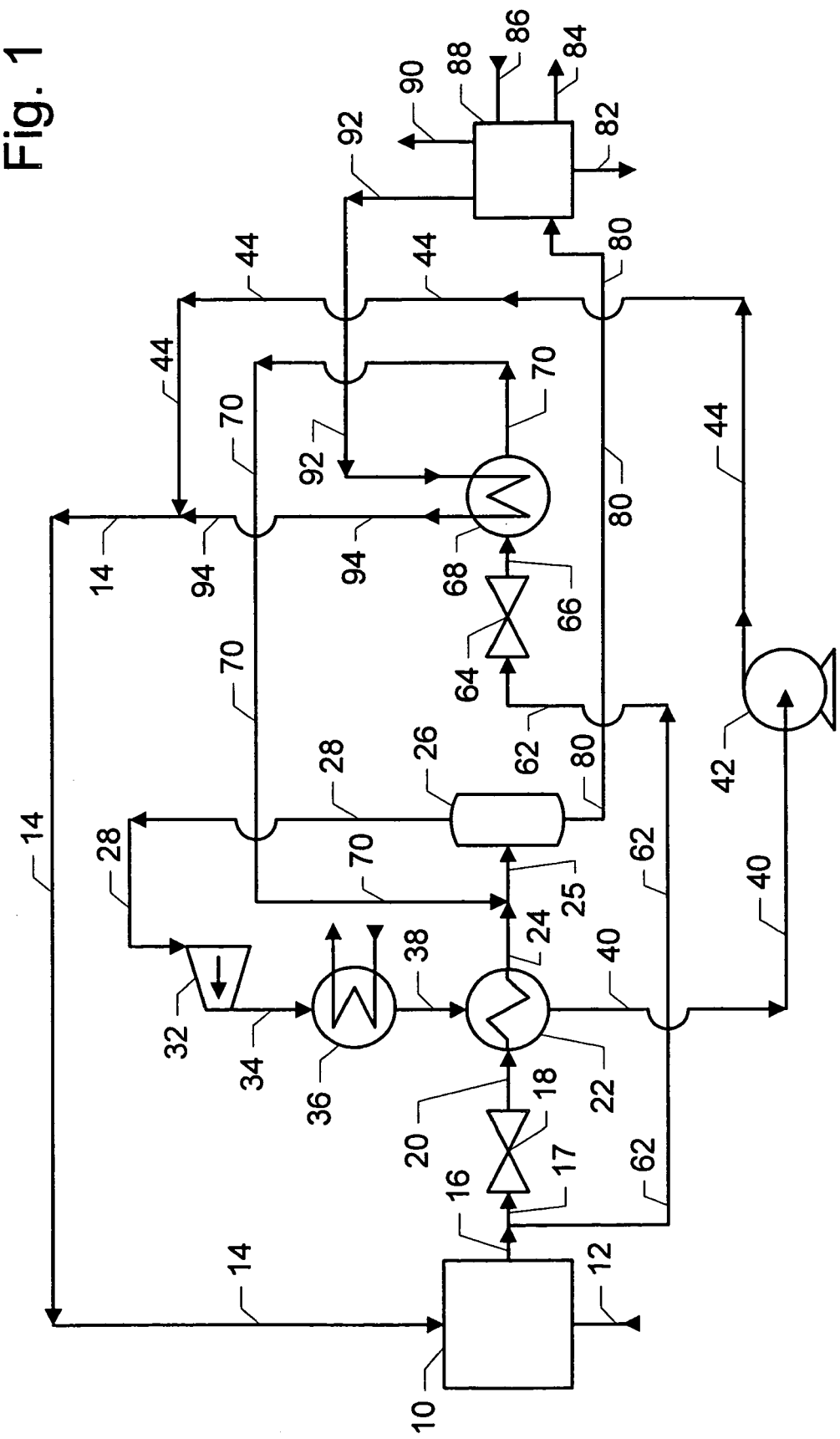
FIGS. 1 and 2 show embodiments of the invention.

The feedstocks for this invention are an alkylation substrate and an alkylating agent. The alkylation substrate is a paraffinic hydrocarbon, such as a branched paraffin having from 4 to 6 carbon atoms. Suitable paraffinic hydrocarbons include 2-methylpropane (commonly called isobutane), 2-methylbutane (or isopentane), 2,3-dimethylbutane, 2-methylpentane, and 3-methylpentane. More than one paraffin may be used.

The alkylation substrate is alkylated with an alkylating agent. The alkylating agent is typically an olefinic hydrocarbon containing from 2 to about 6 carbon atoms. Examples of such olefins include ethylene, propylene, 1-butene, cis-2-butene, trans-2-butene, and iso-butene. More than one olefin may be used.

The alkylation can be performed using any suitable catalyst. Although the alkylation catalyst may be a liquid such as hydrogen fluoride or sulfuric acid, the preferred catalyst is a solid or heterogeneous catalyst. U.S. Pat. No. 6,392,114 B1 (Shields et al.), which is hereby incorporated herein by reference, describes suitable solid catalysts. The process disclosed herein is well-suited generally for a catalyst that comprises a halide. One such catalyst is a refractory inorganic oxide impregnated with a monovalent cation, especially an alkali metal cation or an alkaline earth metal cation, and whose bound surface hydroxyl groups have been at least partially reacted with a Friedel-Crafts metal halide, as described in U.S. Pat. No. 6,392,114 B1. The alkylation reactor may be any suitable alkylation reactor. When the alkylation catalyst is a solid, a transport reactor may be used. U.S. Pat. No. 6,392,114 describes a suitable riser-reactor.

Suitable alkylation conditions include a temperature of from about −50 to about 100° C. (−58 to 212° F.) and a pressure as required to maintain the hydrocarbons present as a liquid. The pressure is in the range of usually from about 1380 to about 4830 kPa(g) (200 to 700 psi(g)). Since an excess of the alkylation substrate is generally provided relative to the alkylating agent, the overall molar ratio of alkylation substrate to alkylating agent is generally from about 5:1 to about 20:1. Injection of the alkylating agent at a number of points in the alkylation reactor may be used to maintain an average molar ratio that is higher than the overall molar ratio. The alkylation reactor may be any suitable reactor such as a riser-reactor. The reactor and reaction conditions are generally chosen to achieve desired values of reactant conversion, product selectivity, and catalyst stability. However, if desired a person of ordinary skill in the art can optimize the selection of these parameters to affect the product recovery and recycling of components.

The alkylation reaction effluent generally contains the desired product of the alkylation (alkylate), byproducts of side reactions, and unreacted alkylation substrate. When alkylating butenes with isobutane, the alkylation reaction effluent typically comprise hydrocarbons having from 1 to 12 carbon atoms, including methane, ethane, propane, propene, butanes, butenes, pentanes, pentanes, hexanes, heptanes, octanes, nonanes, decanes, undecanes, and dodecanes. Depending on the alkylation catalyst, the alkylation reaction effluent may contain a halogen-containing species too. The halogen-containing species is typically present in a concentration of generally greater than about 250 wt-ppm halogen, and is usually from about 1000 to about 10000 wt-ppm halogen, based on the weight of the alkylation reaction effluent. Examples of halogen-containing species include organic halides and hydrogen halides. These species include organic fluorides, organic chlorides, organic bromides, hydrogen fluoride, hydrogen chloride, and hydrogen bromide. Examples of organic halides include the products of halogenating the alkylating agent such as propyl chlorides and butyl chlorides.

In accord with the process disclosed herein, some or all of the alkylation reactor effluent is flashed. That is, its pressure is lowered from the reaction pressure to a lower pressure. Although the flashing preferably occurs at constant enthalpy, the enthalpy of the reactor effluent may change. Since the hydrocarbons in the alkylation reactor effluent are usually in a liquid phase, the flashing typically vaporizes some of the lighter hydrocarbons in the effluent, such as the alkylation substrate. The resulting reactor effluent may thus be a two-phase mixture of vapor and liquid.

The flashing also lowers the temperature of the reactor effluent. Even though the reactor effluent may carry with it some of the heat generated by the alkylation reaction, the temperature of the reactor effluent after the flashing is low enough as to permit some or all of the reactor effluent to be used to cool another stream by indirectly exchanging heat from that stream. That in turn heats the reactor effluent. The stream that is cooled is formed at least in part from a vapor phase which itself is formed by phase separating the reactor effluent after the indirect heat exchange.

The phase separation of the reactor effluent after the indirect heat exchange takes place at a pressure of generally from about 0 to about 483 kPa(g) (0 to 70 psi(g)) and at a temperature of generally from about −9 to about 32° C. (15 to 90° F.). (The pressure could also be subatmospheric, provided that suitable measures to limit or prevent air ingress are taken. However, such measures are usually impractical or uneconomical.) More specifically, those conditions depend in part on the number of times the reactor effluent (or a liquid phase derived therefrom) is flashed enroute from the alkylation reactor to the alkylate product recovery section. Each stage of flashing lowers the pressure and temperature of the stream that is flashed, and therefore it is generally the case that the greater the number of stages, the smaller is the drop in pressure and temperature from stage to stage. Thus, the greater the number of stages, the closer the pressure and temperature of the phase separation of the reactor effluent after the indirect heat exchange is to the pressure and temperature of the alkylation reactor itself. Thus, the phase separation with only a single stage of flashing occurs at a pressure of generally from about 69 to about 207 kPa(g) (10 to 30 psi(g)), preferably from about 103 to about 172 kPa(g) (15 to 25 psi(g)), and at a temperature of generally from about 7 to about 18° C. (45 to 65° F.), preferably from about 10 to about 16° C. (50 to 60° F.). If there are two stages of flashing, this phase separation occurs at a pressure of generally from about 207 to about 414 kPa(g) (30 to 60 psi(g)), preferably from about 241 to about 379 kPa(g) (35 to 55 psi(g)), and at a temperature of generally from about 7 to about 24° C. (45 to 75° F.), preferably from about 10 to about 21° C. (50 to 70° F.). If there are three stages of flashing, this phase separation occurs at a pressure of generally from about 241 to about 483 kPa(g) (35 to 70 psi(g)), preferably from about 276 to about 448 kPa(g) (40 to 65 psi(g)), and at a temperature of generally from about 18 to about 32° C. (65 to 90° F.), preferably from about 21 to about 29° C. (70 to 85° F.). The vapor phase that results from this phase separation is enriched in the alkylation substrate relative to the reactor effluent, and the resultant liquid phase is depleted in the alkylation substrate.

The stream that is cooled by indirect heat exchange with the reactor effluent is sometimes referred to herein as the refrigerant, because it is used in the process disclosed herein in a way similar to how a refrigerant is used in a refrigeration system. The refrigerant, which is formed at least in part from vapor phase from the phase separation, is compressed. After being compressed and prior to being cooled in the indirect heat exchange step, the refrigerant is at least partially condensed using a condenser. Usually the condenser is either a water- or air-cooled heat exchanger, but other coolants for the condenser are possible. For example, the condenser coolant may be the working refrigeration fluid of an external refrigeration unit, or it may be a stream in the product recovery section that requires reboiling.

The indirect heat exchange then itself may partially condense, complete the condensation of, or lower the temperature of, the refrigerant. Any suitable indirect heat exchanger may be used. After the indirect heat exchange step, the temperature of the refrigerant is generally from about 2 to about 11° C. (3 to 20° F.) and preferably from about 3 to about 8° C. (5 to 15° F.) above the temperature of the phase separation of the reactor effluent after the indirect heat exchange. The pressure of the refrigerant is generally sufficient to achieve the desired extent of condensation.

After the indirect heat exchange, the refrigerant is either a two-phase, vapor-liquid mixture containing components that did not condense (partially condensed) or a single liquid phase (totally condensed). Generally, the refrigerant has been chilled by the indirect heat exchange to as low a temperature as can be practically attained. Although the refrigerant contains mostly the alkylation substrate which is almost entirely condensed after the indirect heat exchange, the reactor effluent and hence the refrigerant may contain components that do not condense either in the condensation step or in the indirect heat exchange step. These components have not condensed because their concentration in the refrigerant has risen or is otherwise beyond the level of their solubility in the refrigerant at the conditions of temperature and pressure after the refrigerant has been indirectly heat exchanged with the reactor effluent. These uncondensed components usually have fewer carbon atoms than the alkylation substrate. These uncondensed components comprise most of any vapor phase that is present after the indirect heat exchange step, except for any equilibrium (or near-equilibrium) concentration of the alkylation substrate owing to the vapor phase being in contact with the liquid phase.

In some instances, these uncondensed components in the refrigerant are preferably returned to the alkylation reactor. For example, hydrogen chloride in the refrigerant may not condense at the outlet conditions of the indirect heat exchange step, but if the alkylation takes place in the presence of a chloride-containing solid catalyst it would be preferred that the hydrogen chloride condensed. If the hydrogen chloride would condense, then if the liquid phase is recycled to the alkylation reactor the hydrogen chloride would be returned as well. So, in such a case, preferably the conditions of the refrigerant after the indirect heat exchange are sufficient to keep in solution in the liquid phase at least 99% and more preferably all of the hydrogen chloride in the refrigerant. Any uncondensed hydrogen chloride would be lost from the refrigerant and would have to be replaced by adding makeup chloride to the alkylation reactor, unless it is otherwise recovered and returned to the process.

The optimum amount of condensation for a component in the refrigerant that is preferably returned to the alkylation reactor depends on an economic balancing of the costs of not condensing the component with the costs of condensing the component. The costs of not condensing a component such as hydrogen chloride would include the costs of adding makeup chloride and of disposing of lost hydrogen chloride. These costs are offset by the costs of the high-pressure equipment and of the utilities needed to compress the refrigerant to a sufficiently high discharge pressure to condense the component. A person of ordinary skill in the art can determine this optimum.

In other instances, the uncondensed components in the refrigerant are preferably not returned to the alkylation reactor, as in the case of paraffins lighter than or having fewer carbon atoms than the alkylation substrate. Examples include propane, ethane, and methane when isobutane is the alkylation substrate. Such components are preferably maintained in the vapor phase and are separated from the alkylation substrate by distillation or phase separation prior to recycling the alkylation substrate to the alkylation reactor.

The liquid phase resulting from the phase separation of the alkylation reactor effluent after the indirect heat exchange may itself be flashed and then phase-separated one or more times. Each subsequent flash and phase separation lifts more and more of the alkylation substrate and other components from the liquid phase. So, each resulting vapor phase is enriched in alkylation substrate, and each resulting liquid phase is depleted in alkylation substrate, relative to the liquid phase that is flashed. The resulting vapor phase(s) can be compressed in one or more compression stages and can be ultimately combined with the vapor phase from the initial phase separation of the alkylation reactor effluent. A person of ordinary skill in the art can optimize the number of flashing, phase separation, and compression stages, and their operating conditions, in order to achieve a desired recovery of alkylation substrate and alkylate and with a view toward minimizing utilities costs for a given expenditure in capital equipment. With two stages of flashing (and compression), the second phase separation occurs at a pressure of generally from about 21 to about 117 kPa(g) (3 to 17 psi(g)), preferably from about 55 to about 83 kPa(g) (8 to 12 psi(g)), and at a temperature of generally from about −4 to about 13° C. (25 to 55° F.), preferably from about −1 to about 10° C. (30 to 50° F.). With three stages of flashing, the second phase separation occurs at a pressure of generally from about 138 to about 276 kPa(g) (20 to 40 psi(g)), preferably from about 172 to about 241 kPa(g) (25 to 35 psi(g)), and at a temperature of generally from about 4 to about 18° C. (40 to 65° F.), preferably from about 7 to about 16° C. (45 to 60° F.). With three stages of flashing, the third phase separation occurs at a pressure of generally from about 0 to about 69 kPa(g) (0 to 10 psi(g)), preferably from about 7 to about 34 kPa(g) (1 to 5 psi(g)), and at a temperature of generally from about −9 to about 2° C. (15 to 35° F.), preferably from about −7 to about −1° C. (20 to 30° F.). In this latter case the pressure could be subatmospheric, subject to the earlier comments herein concerning air ingress.

Figure 2:
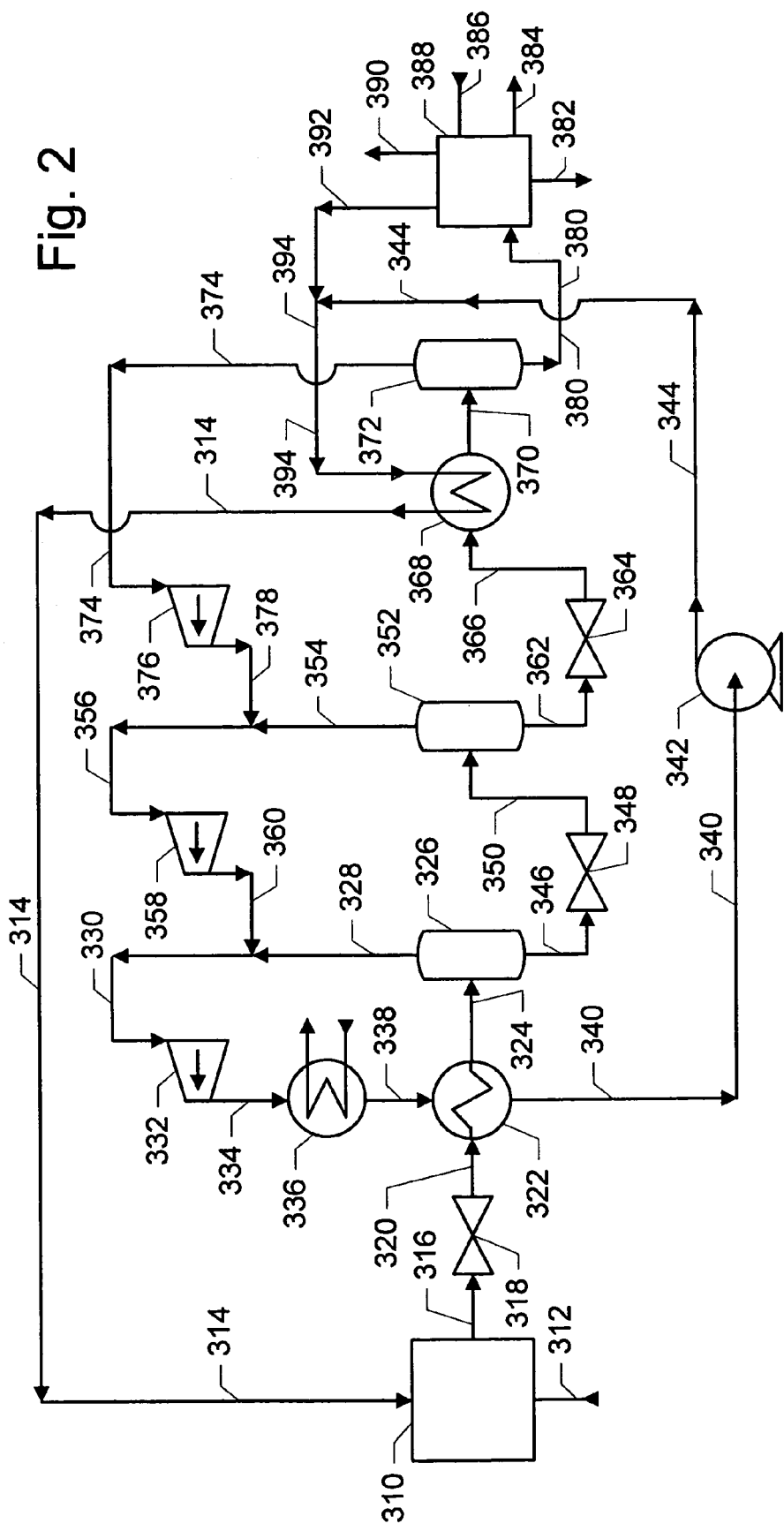

The process disclosed herein can be more fully understood by reference to FIGS. 1 and 2. For clarity and simplicity, some items associated with the operation of the embodiments of the invention have not been shown. These items include flow and pressure control valves, heaters, pumps, compressors, heat exchangers, temperature and pressure monitoring systems, vessel internals, etc., which may be of customary design. FIGS. 1 and 2 are not intended to limit the scope of the invention as set forth in the claims. In addition, the description of FIGS. 1 and 2 is written in terms of isobutane as the alkylation substrate, a mixture of butene isomers as the alkylation agent, and hydrogen chloride as the halogen-containing species in the reactor effluent. However, the choice of these reactants and this halogen-containing species is not intended to limit the scope of the invention as set forth in the claims.

Referring now to FIG. 1, a mixed butenes feedstock enters alkylation reactor 10 through line 12. The butenes may be introduced into the reactor 10 at more than one point. A stream containing fresh and recycle isobutane as the alkylation substrate enters reactor 10 through line 14. The alkylation reactor uses a solid catalyst employing a chloride. The alkylation reactor effluent contains alkylate, isobutane, propane, ethane, methane, and hydrogen chloride. The $C_1$–$C_3$ paraffins may have entered the reactor with the feedstocks or may have been formed as alkylation byproducts. The effluent may even contain some hydrogen due to catalyst regeneration.

The alkylation reactor effluent flows through line 16 and splits into two portions. One portion flows through line 17 and flashes across expansion valve 18, which lowers that portion's pressure and temperature. The flashed portion is a two-phase vapor-liquid mixture that flows through line 20 into refrigerant heat exchanger 22. By indirect heat exchange, the flashed portion removes heat from the stream flowing through line 38, thereby heating this portion of the reactor effluent. The heated portion is still a two-phase vapor-liquid mixture. The flows through line 24, combines with the stream flowing in line 70, flows through line 25, and enters vapor-liquid separator 26. Separator 26 and the other vapor-liquid separators of FIGS. 1 and 2 are cylindrical vertically oriented vessels that may contain internals to assist phase separation. Horizontally oriented vessels and indeed any suitable phase separation device may be used for these vapor-liquid separators. A vapor phase enriched in isobutane and containing propane, ethane, methane, and hydrogen chloride is recovered from separator 26 in line 28. (Hydrogen may be present, but if so it is present only in small quantities compared to hydrogen chloride.) This vapor phase is deemed a refrigerant for the process. Compressor 32 compresses this vapor phase and discharges it into line 34. Water-cooled condenser 36 condenses a portion of the compressed stream in line 34, and a two-phase vapor-liquid mixture flows through line 38 to exchanger 22. In exchanger 22, further condensation of isobutane occurs. The refrigerant is cooled in exchanger 22 to such an extent that, at the pressure of the chilled recycle stream recovered from the outlet of exchanger 22, a significant portion of the hydrogen chloride is condensed and is present dissolved in solution in the isobutane-rich liquid phase in line 40.

The chilled recycle stream flowing in line 40 contains paraffins lighter than the alkylation substrate and/or hydrogen chloride. Hydrogen, if any, is present only in small quantities relative to hydrogen chloride. Since these components do not react to any significant extent in the alkylation reactor, recycling all of the $C_1$–$C_3$ paraffins and hydrogen would allow them to accumulate in the refrigerant to concentrations that are not condensable. These components are preferably purged from the refrigerant from any convenient location. One possibility is to vent a slipstream from line 28. Although this option would save the cost of compressing the slipstream in compressor 32, the compressor suction pressure might be too low as a practical matter for the slipstream to be useful elsewhere. Two other possibilities are to vent a slipstream from lines 34 or 38. While these locations would reject the slipstream at a higher and more useful pressure, they would prevent the slipstream from exchanging its heat with the reactor effluent in exchanger 22, thereby reducing the vaporization of the reactor effluent and thus the flow of refrigerant itself. These two possibilities, however, are not equivalent in terms of the duty of condenser 36. (Condenser 36 and/or exchanger 22 may also have a normally closed vent, which can be opened to remove "noncondensables".) If the chilled recycle stream in line 40 is a two-phase mixture, a fourth possibility is to pass some or all of the stream flowing in line 40 to a vapor-liquid separator (not shown), forming a vapor phase and a liquid phase, rejecting the resulting vapor phase from the process, and routing the resulting liquid phase to pump 42. This would help prevent cavitation in pump 42 and would minimize isobutane losses by concentrating the $C_1$–$C_3$ paraffins and/or hydrogen in the vented stream. On the other hand if the chilled recycle stream in line 40 is a single liquid phase, it may be preferred to pass a slipstream from line 44 to product recovery section 88. There, the slipstream could be charged to a flash drum or a depropanizer distillation column (not shown). The flash drum or depropanizer would concentrate the $C_1$–$C_3$ paraffins and/or hydrogen in its overhead stream to be rejected from the process in line 90, and the isobutane would be recovered in its bottom stream to be recycled to the alkylation reactor 10 through line 92 or through line 12 (by way of a line not shown). The product recovery section 88 could include both a flash drum and a depropanizer. The selection of the optimum from among these options is within the skill of a person of ordinary skill in the art.

Regardless of the location chosen for purging the $C_1$–$C_3$ paraffins and hydrogen chloride, most or all of the refrigerant flows through line 40 and is pumped by pump 42 to the pressure required for charging to either the alkylation reactor 10 or the product recovery section 88. Except for any slipstream to product recovery section 88, pump 42's discharge stream flows through line 44, combines with the stream flowing in line 94, and returns to the alkylation reactor via line 14.

The other portion of the reactor effluent flows through line 62 and flashes across expansion valve 64, which lowers this portion's pressure and temperature. This flashed portion is also a two-phase vapor-liquid mixture that flows through line 66 to exchanger 68. Using indirect heat exchange, this flashed portion of the reactor effluent removes heat from the isobutane-containing recycle stream flowing through line 92. While cooling the recycle stream before its return to the alkylation reactor 10, this heat exchange heats and/or vaporizes some of this portion of the reactor effluent. The effluent of exchanger 68 flows through line 70, combines with the portion of the effluent flowing in line 24, flows through line 25, and enters separator 26.

The liquid phase recovered from separator 26 in line 80 contains alkylate and usually some isobutane too, but it is depleted in isobutane relative to the stream flowing in line 25. This liquid phase flows to product recovery section 88. Although not shown, product recovery section 88 typically consists of the previously mentioned flash drum or depropanizer distillation column as well as a deisobutanizer distillation column (not shown), which is commonly called an isostripper. The liquid phase in line 80 and a field butanes stream, which consists of a mixture of normal butane and isobutane, in line 86 are charged to the isostripper. A normal butane stream in line 84, an alkylate product stream in line 82, and the isobutane stream in line 92 (which contains both fresh isobutane charged via line 86 and recycle isobutane) are recovered from the isostripper. Optionally, some or all of the normal butane may be recovered in line 82.

The isobutane in the stream in line 92 is recycled to the alkylation reactor 10 via exchanger 68, line 94, and line 14. This route cools the recycle and fresh isobutane in exchanger 68 before charging it to alkylation reactor 10. The stream in line 14 is at a temperature of generally from about −4 to about 27° C. (25 to 80° F.). Although not shown in FIG. 1, the streams in lines 92 and 12 may be cooled by heat exchange with some or all of the liquid phase flowing in line 80.

Turning now to FIG. 2, FIG. 2 shows three stages of compression, whereas FIG. 1 shows only one stage. Because FIG. 2 is similar to FIG. 1, similar items in both FIGS. 1 and 2 have been given similar (but not identical) numbering. To avoid needless repetition, these similar items are not described in detail again. The butene feedstock enters reactor 310 through line 312. An isobutane-containing stream enters reactor 310 through line 314. The alkylation reactor effluent flows through line 316 and flashes across valve 318. The resulting vapor-liquid mixture flows through line 320 to refrigerant heat exchanger 322 where it is further vaporized as it cools the stream in line 338. The exchanger effluent flows through line 324 and enters vapor-liquid separator

326. A vapor phase enriched in isobutane and containing $C_1$–$C_3$ paraffins and hydrogen chloride is recovered from separator 326 in line 328. This vapor phase combines with the stream flowing in line 360 to form the stream in line 330, which functions as the refrigerant in the process. Compressor 332 compresses this stream and discharges it into line 334. Water-cooled condenser 336 condenses a portion of the stream in line 334, and a vapor-liquid mixture flows through line 338 to exchanger 322 where essentially complete condensation occurs. All of the hydrogen chloride is in solution in the isobutane-rich liquid phase in line 340.

All of the refrigerant flows through line 340 to pump 342, which pumps the refrigerant into line 344. A line (not shown) carries a slipstream of pump 342's discharge stream from line 344 to product recovery section 388. The bulk of pump 342's discharge stream combines with the stream flowing in line 392, flows through line 394, is cooled in recycle heat exchanger 368, and returns to the alkylation reactor 310 via line 314.

The liquid phase recovered from separator 326 in line 346 contains alkylate and is depleted in isobutane compared to the stream flowing in line 324. The liquid phase flashes across expansion valve 348, which drops the liquid phase's pressure and temperature and forms a two-phase mixture that flows through line 350 to vapor-liquid separator 352. A vapor phase enriched in isobutane and containing methane, ethane, propane, and hydrogen chloride is recovered from separator 352 in line 354. This vapor phase combines with the stream flowing in line 378 to form the stream in line 356. Compressor 358 compresses this stream and discharges it into line 360.

The liquid phase recovered from separator 352 in line 362 contains alkylate and is depleted in isobutane compared to the stream flowing in line 350. The liquid phase flashes across expansion valve 364, which drops the liquid phase's pressure and temperature and forms a two-phase mixture that flows through line 366 to exchanger 368. This flashed liquid phase cools the isobutane-containing stream flowing in line 394 and passes as a vapor-liquid mixture through line 370 to vapor-liquid separator 372. A vapor phase enriched in isobutane and containing methane, ethane, propane, and hydrogen chloride is recovered from separator 372 in line 374. Compressor 376 compresses this stream and discharges it into line 378. A liquid phase containing alkylate and depleted in isobutane is recovered from separator 372 in line 380.

The liquid phase in line 380 flows to product recovery section 388. Line 386 carries a field butanes stream carrying isobutane feedstock to the product recovery section 388. A light stream comprising methane, ethane, propane, and hydrogen chloride is rejected from the process in line 390. A normal butane stream in line 384, an alkylate product stream in line 382, and the isobutane-containing stream (which contains both fresh and recycle isobutane) in line 392 are recovered from the product recovery section.

A variation of the embodiment in FIG. 2 uses two stages of compression. Thus, valve 348, line 350, separator 352, and line 362 are eliminated, so that the stream in line 346 flows directly to valve 364. Line 354, line 356, compressor 358, and line 360 are deleted also, and the stream in line 378 flows to the junction of lines 328 and 330.

What is claimed is:

1. An alkylation process comprising
   a) alkylating an alkylation substrate with an alkylating agent to form alkylate in a reactor;
   b) recovering from the reactor a reactor effluent comprising the alkylate and the alkylation substrate;
   c) flashing at least a portion of the reactor effluent to form a refrigerant exchanger feed comprising the alkylate and the alkylation substrate, wherein the refrigerant exchanger feed has the same composition as the at least a portion of the reactor effluent;
   d) heating at least a portion of the refrigerant exchanger feed in a refrigerant heat exchanger and recovering from the refrigerant heat exchanger a refrigerant exchanger effluent comprising the alkylate and the alkylation substrate;
   e) passing at least a portion of the refrigerant exchanger effluent to an effluent vapor-liquid separator and recovering from the effluent vapor-liquid separator a vapor phase comprising the alkylation substrate and a liquid phase comprising the alkylate;
   f) compressing the vapor phase to form a compressed stream comprising the alkylation substrate;
   g) at least partially condensing at least a portion of the compressed stream to form a condensed stream comprising the alkylation substrate;
   h) indirectly exchanging heat in the refrigerant heat exchanger from at least a portion of the condensed stream to the at least a portion of the refrigerant exchanger feed to form a chilled recycle stream comprising the alkylation substrate;
   i) recycling at least a portion of the chilled recycle stream to the reactor; and
   j) recovering the alkylate from the liquid phase.

2. The process of claim 1 further characterized in that the at least a portion of the condensed stream at least partially condenses in the refrigerant heat exchanger, the chilled recycle stream comprises a condensed phase, and the recycling of the at least a portion of the chilled recycle stream comprises recycling the condensed phase.

3. The process of claim 2 further characterized in that the chilled recycle stream comprises a hydrogen halide, and the condensed phase comprises at least 99% of the hydrogen halide in the chilled recycle stream.

4. The process of claim 3 wherein the hydrogen halide comprises hydrogen chloride.

5. The process of claim 1 further characterized in that the alkylating occurs in the presence of a solid catalyst.

6. The process of claim 1 wherein the reactor is a transport reactor.

7. The process of claim 6 wherein the transport reactor is a riser-reactor.

8. The process of claim 1 further characterized in that the at least a portion of the refrigerant exchanger effluent is separated at separation conditions comprising a pressure of from about 0 to about 483 kPa(g) and a temperature of from about −9 to about 32° C.

9. The process of claim 1 further characterized in that the effluent vapor-liquid separator operates at a phase separation temperature and the chilled recycle stream is at a chilled recycle temperature of from about 2 to about 11° C. greater than the phase separation temperature.

10. The process of claim 1 further characterized in that the vapor phase comprises a light component having fewer carbon atoms than the alkylation substrate, a reject stream comprising the light component is formed from a stream selected from the group consisting of the vapor phase, the compressed stream, the condensed stream, and the chilled recycle stream, and the light component in the reject stream is rejected from the process.

11. The process of claim 1 further characterized in that the at least a portion of the refrigerant exchanger feed comprises a hydrogen halide.

12. An alkylation process comprising
a) alkylating an alkylation substrate with an alkylating agent to form alkylate in a reactor;
b) recovering from the reactor a reactor effluent comprising the alkylate and the alkylation substrate;
c) depressuring at least a portion of the reactor effluent, wherein the at least a portion of the reactor effluent after the depressuring has the same composition as the reactor effluent;
d) heating the at least a portion of the reactor effluent after the depressuring in a refrigerant heat exchanger and recovering from the refrigerant heat exchanger a refrigerant exchanger effluent comprising the alkylate and the alkylation substrate;
e) passing at least a portion of the refrigerant exchanger effluent to an effluent vapor-liquid separator and recovering from the effluent vapor-liquid separator a vapor phase comprising the alkylation substrate and a liquid phase comprising the alkylate;
f) compressing the vapor phase to form a compressed stream comprising the alkylation substrate;
g) at least partially condensing at least a portion of the compressed stream to form a condensed stream comprising the alkylation substrate;
h) indirectly exchanging heat in the refrigerant heat exchanger from at least a portion of the condensed stream to the at least a portion of the reactor effluent to form a chilled recycle stream comprising the alkylation substrate;
i) recycling at least a portion of the chilled recycle stream to the reactor; and
j) recovering the alkylate from the liquid phase.

* * * * *